United States Patent [19]

Berlanga Barrera

[11] Patent Number: 5,820,541

[45] Date of Patent: Oct. 13, 1998

[54] PROCESS, FORMULA AND INSTALLATION FOR THE TREATMENT AND STERILIZATION OF BIOLOGICAL, SOLID, LIQUID, FERROUS METALLIC, NON-FERROUS METALLIC, TOXIC AND DANGEROUS HOSPITAL WASTE MATERIAL

[75] Inventor: Manuel Berlanga Barrera, Valencia, Spain

[73] Assignee: Biozon, S.L., Valencia, Spain

[21] Appl. No.: 682,685

[22] PCT Filed: Nov. 14, 1995

[86] PCT No.: PCT/ES95/00126

§ 371 Date: Dec. 26, 1996

§ 102(e) Date: Dec. 26, 1996

[87] PCT Pub. No.: WO96/14884

PCT Pub. Date: May 23, 1996

[30] Foreign Application Priority Data

Nov. 15, 1994 [ES] Spain ................................ 9402346

[51] Int. Cl.⁶ ................................ A62D 3/00; B09B 3/00
[52] U.S. Cl. ................................ 588/258; 210/173; 210/192; 210/195.1; 210/760; 210/764; 241/DIG. 38; 405/128; 422/28; 422/32; 588/900
[58] Field of Search ................................ 588/249, 258, 588/900; 210/173, 192, 195.1, 760, 764; 241/DIG. 38; 405/128; 422/28, 32

[56] References Cited

U.S. PATENT DOCUMENTS

| 3,549,528 | 12/1970 | Armstrong . | |
|---|---|---|---|
| 3,847,803 | 11/1974 | Fisk | 210/760 X |
| 5,078,965 | 1/1992 | Pearson | 210/760 X |
| 5,116,574 | 5/1992 | Pearson | 210/760 X |
| 5,173,257 | 12/1992 | Pearson | 422/28 X |
| 5,520,888 | 5/1996 | Berndt | 210/760 X |
| 5,591,117 | 1/1997 | Zelno | 588/258 |

FOREIGN PATENT DOCUMENTS

| 3121686 | 12/1982 | Germany . |
| 1-076860 | 6/1989 | Japan . |
| WO 91/12889 | 9/1991 | WIPO . |
| WO 92/17275 | 10/1992 | WIPO . |

Primary Examiner—George A. Suchfield
Attorney, Agent, or Firm—Klauber & Jackson

[57] ABSTRACT

A process, formula and apparatus for the treatment and sterilization of biological, solid, liquid, ferrous metallic, non-ferrous metallic, toxic and hospital dangerous waste or residual material utilizes a mixture of oxygen, ozone, water, and optionally, carbon dioxide, in variable proportions and rates. The apparatus comprises an oxygen container (10) and a carbon dioxide container (11) from which the oxygen and the carbon dioxide are incorporated through respective conduits (13) and (15) to an ozonizer (1) provided with cooling water inlet (16) and outlet (17). The conduits (13) and (15) exit adjacent to the ozone conduit (14), up to the injector (3), and are actuated by the pump (2) and pass through the mixing conduit (4) to the absorption and outgassing tank (5) from which the conduit (6) for the washing fluid passes to the treatment tank (7) having a degasification valve (12) or catalyst. The waste is thus subjected to a continuous bath with permanent recirculation of the water containing the formula through the conduit line, with subsequent centrifugation, the remaining waste being finally sterilized.

9 Claims, 2 Drawing Sheets

PROCESS, FORMULA AND INSTALLATION FOR THE TREATMENT AND STERILIZATION OF BIOLOGICAL, SOLID, LIQUID, FERROUS METALLIC, NON-FERROUS METALLIC, TOXIC AND DANGEROUS HOSPITAL WASTE MATERIAL

This application is a 35 U.S.C. §371 filing of PCT Application PCT/ES95/00126.

BACKGROUND OF THE INVENTORY FIELD

This invention is applicable within the industry dedicated to the production of apparatus and processes and the installation thereof for the treatment and sterilization of biological wastes in general, and especially those originating from hospitals.

DESCRIPTION OF THE PRIOR ART

The methods known and existing at present for the treatment of solid, liquid, ferreous metal, non-ferreous metal, toxic and biological residues in hospitals are carried out by means of steam autoclaves or by microwaves. All these means suffer from important drawbacks because, the solid, liquid, ferreous metal, non-ferreous metal, toxic and dangerous biological hospital residue, include solids such as dressings, syringes, plungers, glass tubes, glass plates, catheters, stylets, bacteriological culture plates, human body partes, needles, ferreous metals, non-ferreous metals and various other materials contaminated by bacteria and viruses.

The materials and elements mentioned above include semisolid residues, for example, purulents, blood, feces, etc. These materials are highly contaminating and very dangerous, and, consequently, require not only disinfection, but also sterilization. Without sterilization these solid, liquid, ferreous metallic, non-ferreous metallic, toxic and dangerous biological hospital wastes would be deposited in the rubbish dumps and the bacteria and viruses which have survived, under the conditions of humidity and temperature of the rubbish dumps, would reproduce. The autoclave and microwave systems clean, but do not solve the real problem of the elimination of wastes, which are converted into an extremely hazardous material for the transmission of contagious illnesses to humans, animals and water supplies and are thus capable of creating widespread epidemics.

At present, the obvious solution to this problem would be a formula process, and apparatus capable of solving this problem situation, by designing a process together with apparatus and the installations thereof operable in the process.

SUMMARY OF THE INVENTION

The present invention concerns a process, formulation and the installation thereof for the treatment and sterilization of biological, solid, liquid, ferreous metallic, non-ferreous metallic, toxic and dangerous hospital waste material, that is based on a formulation and its use in an appropriate apparatus, to obtain the proposed aim, which offers advantages and improvements over the currently existing systems.

BRIEF DESCRIPTION OF THE DRAWINGS

To complement the description that of the instant process and in order to provide a better understanding of the characteristics of the invention, attached to the present Specification, and forming an integral part of the same, are two pages of drawings in which, in an illustrative and non-limitative manner, the following has been represented.

Figure 1:
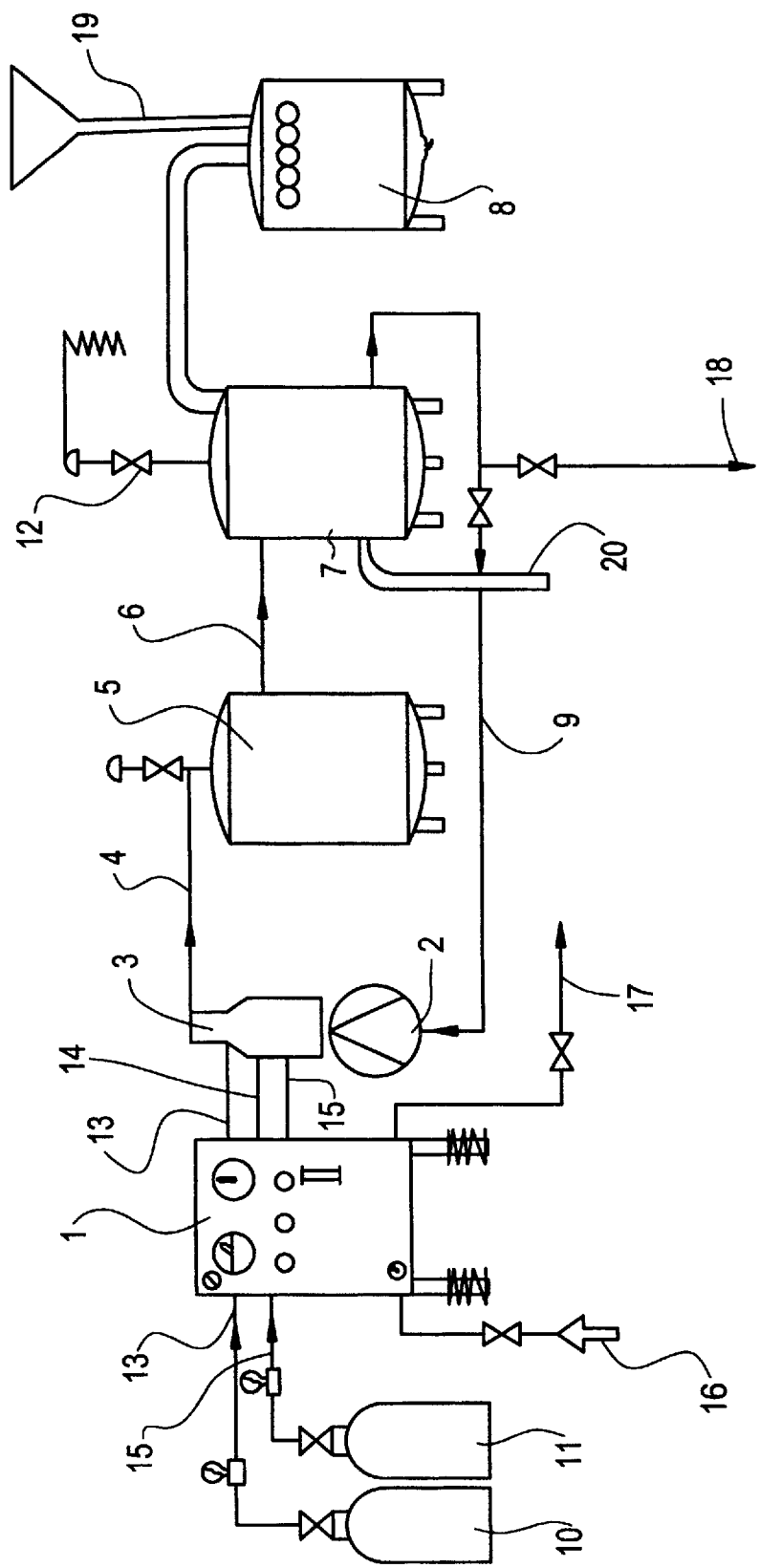
FIG. 1 is a schematic view of the different elements of the equipment which is used in the process formula and apparatus for the treatment and sterilization of the solid, liquid, ferreous metallic, non-ferreous metallic, toxic and dangerous biological hospital waste.
Figure 2:
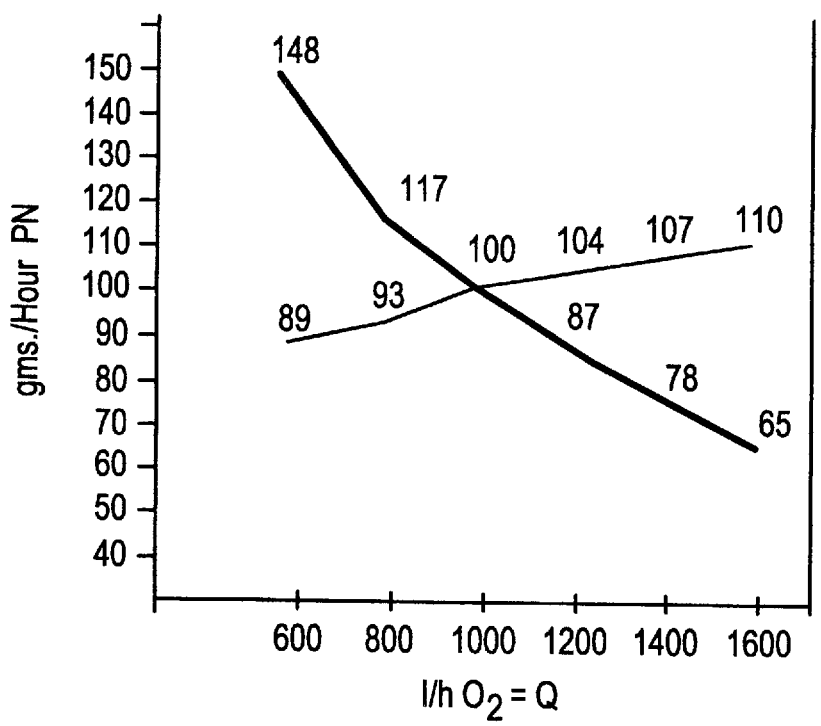
FIG. 2 is a graph of the mixture of the gasses in a base of 100 carried out in a pilot plant. The gas mixture is given by the formula $$PN = \frac{Q_1 \times Q}{1000}$$

wherein PN is the nominal production in grams/hour. $Q_1$ is the concentration of ozone ($O_3$) in grams/m$^3$, and the Q is the flow rate of oxygen ($O_2$) in liters/hour.

DESCRIPTION OF THE INVENTION

The process, formula and apparatus for the treatment and sterilization of solid, liquid, ferreous metallic, non-ferreous metallic, toxic and dangerous biological hospital wastes proposed by the invention results in the total and absolute sterilization of the solid, liquid, ferreous metallic, non-ferreous metallic, toxic and dangerous biological hospital wastes, by changing them to local waste residues devoid of risks.

More specifically, the process, formula and apparatus for the treatment and sterilization of solid, liquid, ferreous metallic, non-ferreous metallic, toxic and dangerous biological hospital wastes, which are the objects of the invention, includes the introduction of such wastes into a mill as part of the apparatus's assembly, with the purpose of destroying all plastic components, syringes, syringe plungers, ferreous metals, non-ferreous metals, test tubes, bacteria culture plates, glass materials and other solids which might exist, as well as to achieve the fragmentation and dissolution of the semisolid residues which are contained in the gauze and the dressings. The crushed material is then contacted with the qualitative formulation of $H_2O+O_2+O_3+CO_2$, and which, when then deposited in domestic waste dumps, cannot be reused.

Subsequently to the pulverizing/grinding operation and to the reduction of the biological wastes by the grinding of the solid, liquid, ferreous metallic, non-ferreous metallic, toxic and dangerous hospital wastes, the crushed material is inserted in a washing and centrifuging machine containing water, bathing these residues and dissolving the blood, semisolid, purulents, human body parts, etc., so as to be in good condition to receive the treatment that, with the formulation of compressed air, ozone, carbon dioxide, these gasses being combined by an ozone generator apparatus.

The ozone and the oxygen, and optionally the carbon dioxide is passed to a primary injector adjusted by a pressure switch. These gasses are mixed with the water which is supplied by the pump. Then, in the first stage, the water with the dissolved gasses, passes through a conduit to an absorption and outgassing tank, and from this tank through another conduit to the washing and centrifuging matching, which contains the toxic and dangerous biological residues. Then the whole device starts working, carrying out a recirculation of the $H_2O+O_2+O_3+CO_2$, so that the residues are exposed to a continuous bath in permanent circulation, with a contact time which ranges from thirty seconds to forty-eight hours. After this period of time for treatment has elapsed, the solid, liquid, ferreous metallic, non-ferreous metallic, toxic and dangerous biological hospital residues are centrifuged and the treatment water is separated. The sterilized residues having been changed to local wastes, are removed from the washing and centrifugal machine and deposited in domestic or local rubbish containers.

In order to determine the antibacterial and virus destroying activity of the formula used in the treatment and sterilization of solid, liquid, ferreous metallic, non-ferreous metallic, toxic and dangerous biological hospital residues, different tests have been conducted, among others, the following studies. These include:

Study of the antibacterial activity of ozone issued by the Microbiological Department of the School of Medicine in the "Universidad Complutense" of Madrid.

Study of the antibacterial activity of ozonized water, issued by the Microbiological Department of the Murica University School of Medicine.

Study on the antibacterial activity ozone, issued by the Social Health Welfare Office of the Castille-La Mancha-Board of Communities.

Study on the bacterial activity of ozone, issued by the "Servel Valencia de Salut", in the "La Fe" hospital, of the "Sanitate and Consume Conselleria" at the Generallat of Valencia.

Study of ozone in the destruction of spores "issued by the Kosib, S.A. Clinical Analysis Laboratories, by Drs. J. Azner, J. Baguena, M. Gobernado and V. Seco.

Essentially, the process of the present invention is a sterilization system of solid, liquid, ferreous metallic, non-ferreous metallic, toxic and dangerous biological hospital residues, whose base of operation is physical-chemical beginning with $O_2$ (oxygen), $O_3$ (ozone), $CO_2$ (carbon dioxide), $H_2O$ (water), whose description of operation, formulation of the gasses and its proportion and mechanic, consists in the formulation $O_2$ (oxygen)+$O_3$ (ozone)+$H_2O$ (water)// $O_2$ (oxygen)+$O_3$ (ozone)+$CO_2$ (carbon dioxide)+$H_2O$ (water), with the following proportions, i.e., $O_2$ (oxygen), from 0.01 liters hour to 100 kilograms/hour;

$O_3$ (ozone), from 0.01 grams hour to 50 kilograms/hour;

$CO_2$ (carbonic dioxide), from 0.01 grams to 50 kilograms/hour;

$H_2O$ (water), from 0.01 liters to 1000 cubic meters/hour.

Applying the process and formulation that has been previously described, the results can be summarized as follows:

Formulation applied: $H_2O+O_2+O_3+CO_2$;

Water flow: $H_2O$=500 liters/hour to recirculation;

Oxygen flow: 1 cubic meter/hour;

Nominal production of ozone: 100 grams hour;

Concentration of ozone: 135 grams cubic meter;

Carbon dioxide flow: 0.2 cubic meters/hour;

Temperature: 181° C.;

pH 7.3.

PREFERRED EMBODIMENT OF THE INVENTION

From FIG. 1, it may be observed how the process, formula and apparatus for the treatment and sterilization of the solid, liquid, ferreous metallic, non-ferreous metallic, toxic and dangerous biological hospital residues are produced from an ozonizer (1), a pump (2), and injector (3) that acts in the first step, as a conductor (4) of mixture $H_2O+O_2+O_3+CO_2$ (first step), to an absorption and outgassing tank (5) (second step).

The invention has an homogenized flow of water $H_2O+O_2+O_3+CO_2$ and a washing tank.

As hereinbefore stated in the description, the invention comprises introduction of the wastes in a conduit (19) into the crushing mill (8), as well as a recirculation conduit (9) for $H_2O$ for the recuperation of the formula, a container (10) of $O_2$ (oxygen), a container (11) of $CO_2$ (carbon dioxide), a valve (12) from outgassing to catalyst, a conduit (13) Of $O_2$ (oxygen)+$O_3$ (ozone), a conduit (14) of $O_3$ (ozone)+$O_2$ (oxygen), a conduit (15) of $CO_2$ (carbon dioxide), an inlet of cooling water (16), an output of cooling water (17), and a drain (18).

The performance and application which is the object of the present invention for the treatment and sterilization of the solid, liquid, ferreous metallic, non-ferreous metallic, toxic and dangerous biological hospital wastes, is conducted by means of compressed oxygen originating from the atmospheric air, or from containers (11) the characteristics of which have been described previously, so as to pass through an ozone generator apparatus (1).

The ozone and the oxygen, and optionally the carbon dioxide is passed to a primary injector (3) adjusted by a pressure switch, mixing these gases with the water (6) which is supplied by a pump (2), and subsequently, this water (6) containing the dissolved gases is a first stage, passes through a mixture system (4) which introduces it to an absorption and outgassing tank (5), and once these stages have been carried out, the water ($H_2O$) plus the gases, oxygen ($O_2$) ozone ($O_3$) and carbon dioxide ($CO_2$) are introduced in the washing and centrifuging machine (7) that contains the solid, liquid, ferreous metallic, non-ferreous metallic, toxic and dangerous biological residues coming from the crushing mill (8), and subsequently the crushed wastes are exposed to a continuous bath by the permanent recirculation (9) of the water, with a contact time which ranges from a second to forty-eight hours. After this period of time for treatment has elapsed, the treatment water is prepared and then a centrifuging is carried out.

Preferably, the process involves transferring ozone and oxygen from the ozonizer to the injector so that the injector transferring ozone and oxygen from the ozonizer to the injector so that the injector receives a mixture of ozone approximately 20% ozone, and thereafter passing the mixture of ozone and oxygen through the second conduit to the absorption and outgassing tank (5), where about 80% of the mixture is dissolved in water, and subsequently, through the third conduit (6) to the treatment tank (7) where a dissolution of 100% of the mixture of ozone and oxygen in water is obtained.

Since the residues are now sterilized and, consequently, changed to local wastes, they are then removed from the machine by a discharge (20) and deposited in domestic or urban containers, and the water also being sterile is poured into the sewer drainage system.

A more extensive description is not considered necessary in order that many expert in the technique may understand the scope of the invention and the advantages derived from the same.

The materials from size and arrangement of the elements shall be susceptible of modification, so long as this does not imply change in the essential characteristics of the invention. The terms utilized herein must always be taken to be of non-limiting character.

I claim:

1. A process for the treatment and sterilization of biological, solid, liquid, ferrous metallic, non-ferrous metallic, toxic hospital residues, comprising the steps of:

(a) crushing the residues in a mill (8);

(b) transferring the crushed residues from the mill (8) to a treatment tank (7) filled with water which has been mixed with oxygen ($O_2$) and ozone ($O_3$) by means of an injector, thereby providing an oxygen-ozone-water mixture, comprising water, oxygen and ozone in the following proportions:

from $10^{-2}$ liters to $10^5$ liters of oxygen;
from $10^{-2}$ liters to $5 \times 10^4$ grams ozone; and
from $10^{-2}$ to $10^6$ liters of water;

(c) recirculating said oxygen-ozone-water mixture of said treatment tank (7) through a system comprising:

the treatment tank (7);
a first conduit (9) for recirculation of the oxygen-ozone-water mixture
a pump (2);
an injector (3);
a second conduit (4) for transferring the oxygen-ozone-water mixture
from the injector (3) to an absorption and outgassing tank (5);
a third conduit (6) for transferring the oxygen-ozone-water mixture from the absorption and outgassing tank (5) to the treatment tank (7);
whereby the residues in the treatment tank (7) are in contact with said oxygen-ozone-water-mixture during the recirculation; and (d) subjecting the residues to contact with said oxygen-ozone-water mixture under recirculation for a contact time period of 1 second to 48 hours; while keeping the mixture at a substantially neutral pH.

2. The process according to claim 1 wherein the temperature of the oxygen-ozone-water mixture at 181° C.

3. The process according to claim 1 wherein the contact time period is from 30 seconds to 48 hours.

4. The process according to claim 1 wherein the contact time period is from 15 to 60 minutes.

5. The process according to claim 1 wherein carbon dioxide ($CO_2$), is added to the oxygen-ozone-water mixture to afford a mixture of water, oxygen, ozone and carbon dioxide in the following proportions:

from $10^{-2}$ to $10^6$ liters of oxygen;
from $10^{-2}$ grams to $5 \times 10^4$ grams ozone; and
from $10^{-2}$ to $10^6$ liters of water;
from $10^{-2}$ grams to $5 \times 10^4$ grams carbon dioxide.

6. The process according to claim 1 wherein the ozone is supplied by an ozonizer (1).

7. The process according to claim 1 wherein transferring ozone and oxygen from the ozonizer to the injector so that the injector receives a mixture of ozone approximately 20% ozone, and thereafter passing the mixture of ozone and oxygen through the second conduit to the absorption and outgassing tank (5), where about 80% of the mixture is dissolved in water, and subsequently, through the third conduit (6) to the treatment tank (7) where a dissolution of 100% of the mixture of ozone and oxygen in water is obtained.

8. The process according to claim 1 wherein said substantially neutral pH is 7.3.

9. The process according to claim 1, please also consider the possibility of filing additional claims relating to the installation, with "means" features corresponding to the different features of the method claims mentioned above.

\* \* \* \* \*

UNITED STATES PATENT AND TRADEMARK OFFICE
CERTIFICATE OF CORRECTION

PATENT NO. : 5,820,541
DATED : October 13, 1998
INVENTOR(S) : Manuel Berlanga Barrera It is certified that error appears in the above-indentified patent and that said Letters Patent is hereby corrected as shown below:

Please delete Claim 9.

Signed and Sealed this

Eighth Day of June, 1999

*Attest:*

Q. TODD DICKINSON

*Attesting Officer*     Acting Commissioner of Patents and Trademarks